(12) United States Patent
Gadsby et al.

(10) Patent No.: US 7,742,828 B2
(45) Date of Patent: Jun. 22, 2010

(54) MEDICAL ELECTRODE SUITABLE FOR HIGH-ENERGY STIMULATION

(75) Inventors: Peter Gadsby, Broomfield, CO (US); Peter F. Meyer, Shrewsbury, MA (US); Scott Coggins, Palmer, MA (US)

(73) Assignee: Tyco Healthcare Group LP, Mansfield, MA (US)

( * ) Notice: Subject to any disclaimer, the term of this patent is extended or adjusted under 35 U.S.C. 154(b) by 839 days.

(21) Appl. No.: 11/541,110

(22) Filed: Sep. 29, 2006

(65) Prior Publication Data
US 2008/0082153 A1  Apr. 3, 2008

(51) Int. Cl.
*A61N 1/05* (2006.01)

(52) U.S. Cl. .................. 607/142; 607/152; 607/148

(58) Field of Classification Search .............. 607/142, 607/149, 152; D24/168
See application file for complete search history.

(56) References Cited

U.S. PATENT DOCUMENTS

| 5,356,428 A * | 10/1994 | Way .................. 607/142 |
| 5,571,165 A | 11/1996 | Ferrari |
| 5,733,324 A | 3/1998 | Ferrari |
| 5,824,033 A | 10/1998 | Ferrari |
| 6,600,957 B2 | 7/2003 | Gadsby |
| 6,745,082 B2 * | 6/2004 | Axelgaard .................. 607/142 |
| 6,898,465 B2 | 5/2005 | Gadsby et al. |
| 2003/0078646 A1 | 4/2003 | Axelgaard |
| 2005/0251241 A1 * | 11/2005 | Axelgaard .................. 607/142 |

FOREIGN PATENT DOCUMENTS

| WO | WO 01/58522 A | 8/2001 |
| WO | WO 02/36002 A | 5/2002 |
| WO | WO 2005/092430 A | 10/2005 |

* cited by examiner

*Primary Examiner*—Kennedy J Schaetzle
(74) *Attorney, Agent, or Firm*—Lisa E. Winsor, Esq.

(57) ABSTRACT

A medical electrode, and a method of making a medical electrode. The electrode comprises an electrode member having a top face and a bottom face; disconnected regions of electrically conductive material in electrical contact with the top face of the electrode member, patient contacting layer and an electrical connector in electrical contact with the disconnected regions. The disconnected regions reduce patient skin irritation and burning while optimizing electrical impedance of the electrode.

24 Claims, 3 Drawing Sheets

MEDICAL ELECTRODE SUITABLE FOR HIGH-ENERGY STIMULATION

TECHNICAL FIELD

The present invention relates generally to medical electrodes and, more particularly, to disposable medical electrodes intended for high-energy stimulation, such as defibrillation.

BACKGROUND OF THE INVENTION

Medical electrodes provide an electrical interface between a patient and monitoring equipment (e.g., an electrocardiograph device) or between a patient and stimulating equipment (e.g., interferential and iontophoresis devices). A specific type of stimulating electrode, used to provide an electrical interface between a patient and defibrillation equipment, must be capable of conducting the high-energy level required for transcutaneous defibrillation.

In a malady called "fibrillation," the normal contractions of a muscle are replaced by rapid, irregular twitchings of muscular fibers (or fibrils). Fibrillation commonly occurs in the atria or ventricles of the heart muscle; the normal, rhythmical contractions of the heart are replaced by rapid, irregular twitchings of the muscular heart wall. A remedy for fibrillation is called "defibrillation," a procedure which applies an electric shock to arrest the fibrillation of the cardiac muscle (atrial or ventricular) and restore the normal heart rhythm.

Defibrillation electrodes deliver high-energy levels required for defibrillation, up to 360 Joules or more. Defibrillation electrodes also distribute the energy over a relatively large area of the epidermis of the patient to achieve adequate current density distribution within the atria or ventricles. Well-defined industry standards exist for defibrillation electrodes. In particular, the American National Standards Institute (ANSI) standards for defibrillation electrodes have been published by the Association for the Advancement of Medical Instrumentation (AAMI). The ANSI standards for the size of defibrillation electrodes recommend, for example, that the minimum active area of individual, self-adhesive electrodes used for adult defibrillation and pacing shall be at least 50 $cm^2$ and that the total area of the two electrodes shall be at least 150 $cm^2$.

The specification for defibrillation recovery characteristics, which describes certain time-related, electrical dissipation properties of the electrode following repeated electrical shocks of defibrillation currents, is difficult for many electrodes to meet. The use of non-compliant electrode may result in life-threatening delays following defibrillation. This restriction limits the usefulness of such electrodes in a critical care environment. Accordingly, many of these products bear a caution label that they are not to be used where defibrillation is a possibility.

Irritation and burning of the patient's skin due to high current density around the perimeter of the electrodes and uneven current distribution is a common problem with defibrillation electrodes, particularly after application of repeated high-level defibrillation or cardiac pacing pulses. A new disposable medical electrode, particularly useful for high-energy applications, is disclosed here. The invention provides an electrode that features control of current distribution. In addition, the electrode provides energy sufficient for defibrillation, and which has improved current distribution between the electrode and the skin surface of the patient to efficiently deliver the energy without burning the patient's skin.

SUMMARY OF THE INVENTION

In one embodiment the electrode comprises an electrically conductive electrode member with a top face and a bottom face. A pattern of disconnected regions of electrically conductive material is disposed on at least a portion of the top face of the electrode member. An electrical connector contacts the discontinuous pattern for delivering energy to and transmitting energy from the electrode. A patient contacting layer is disposed on at least a major portion of the bottom face of the electrode member. An electrically conductive coating may cover at least a portion of the bottom face of the electrode member, between the electrode member and the hydrogel.

Both the foregoing general description and the following detailed description are exemplary, but are not restrictive, of the invention.

BRIEF DESCRIPTION OF THE DRAWINGS

The invention is best understood from the following detailed description when read in connection with the accompanying drawings. It is emphasized that, according to common practice, the various features of the drawing are not to scale. On the contrary, the dimensions of the various features are arbitrarily expanded or reduced for clarity. Included in the drawings are the following figures.

DETAILED DESCRIPTION OF THE INVENTION

Figure 1:
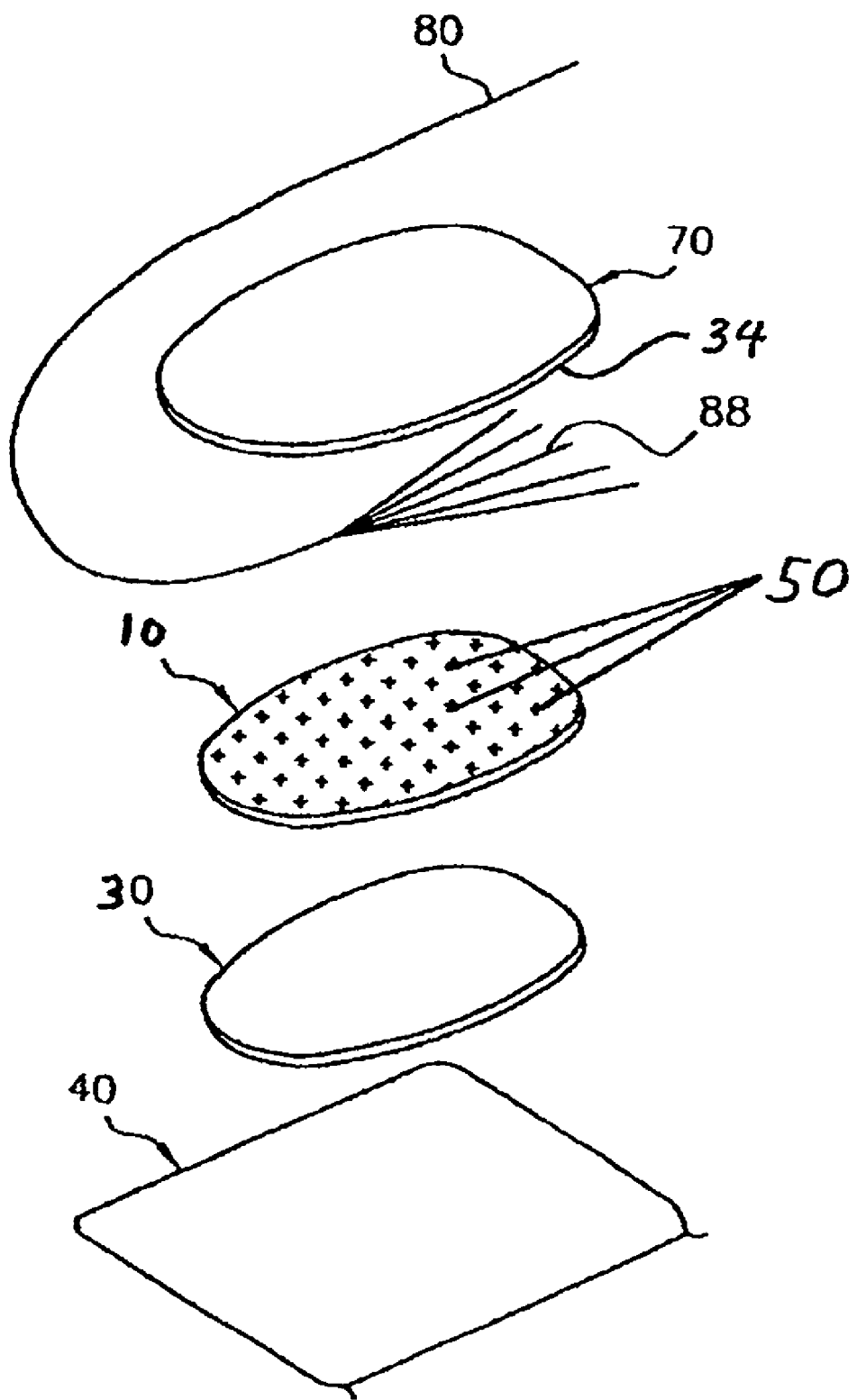
FIG. 1 is a perspective exploded view illustrating the components of a medical electrode according to a first embodiment.

Referring now to the drawing, wherein like reference numbers refer to like elements throughout, the various embodiments of the present invention will be explained in detail.

As illustrated in FIG. 1, the electrode has a release carrier sheet 40. Release carrier sheet 40 covers and protects a patient contacting layer 30, which may comprise an electrically conductive gel layer, a gel pad containing electrically conductive gel, or an electrically conductive adhesive. The release carrier sheet 40 may be made, for example, of silicone-coated polyethylene terephthalate (PET). Although not required, a rectangular shape is suitable for the release carrier sheet 40. If rectangular as illustrated, dimensions such as a length of about 140 mm and a width of about 82 mm are suitable.

In one embodiment, the patient contacting layer 30 comprises a pad of electrically conductive gel in contact with the release cover sheet 40 prior to the use of the electrode. The gel pad may be approximately 65 mm wide and 122 mm long. The gel pad may comprise a skin compatible conductive hydrogel or adhesive having good ability to retain moisture content and adhesive tack. Examples of suitable hydrogels include conductive hydrogels commercially available from the Kendall-LTP division of Tyco Healthcare Group LP, Mansfield, Mass., such as RG-63B conductive hydrogel.

Figure 2:
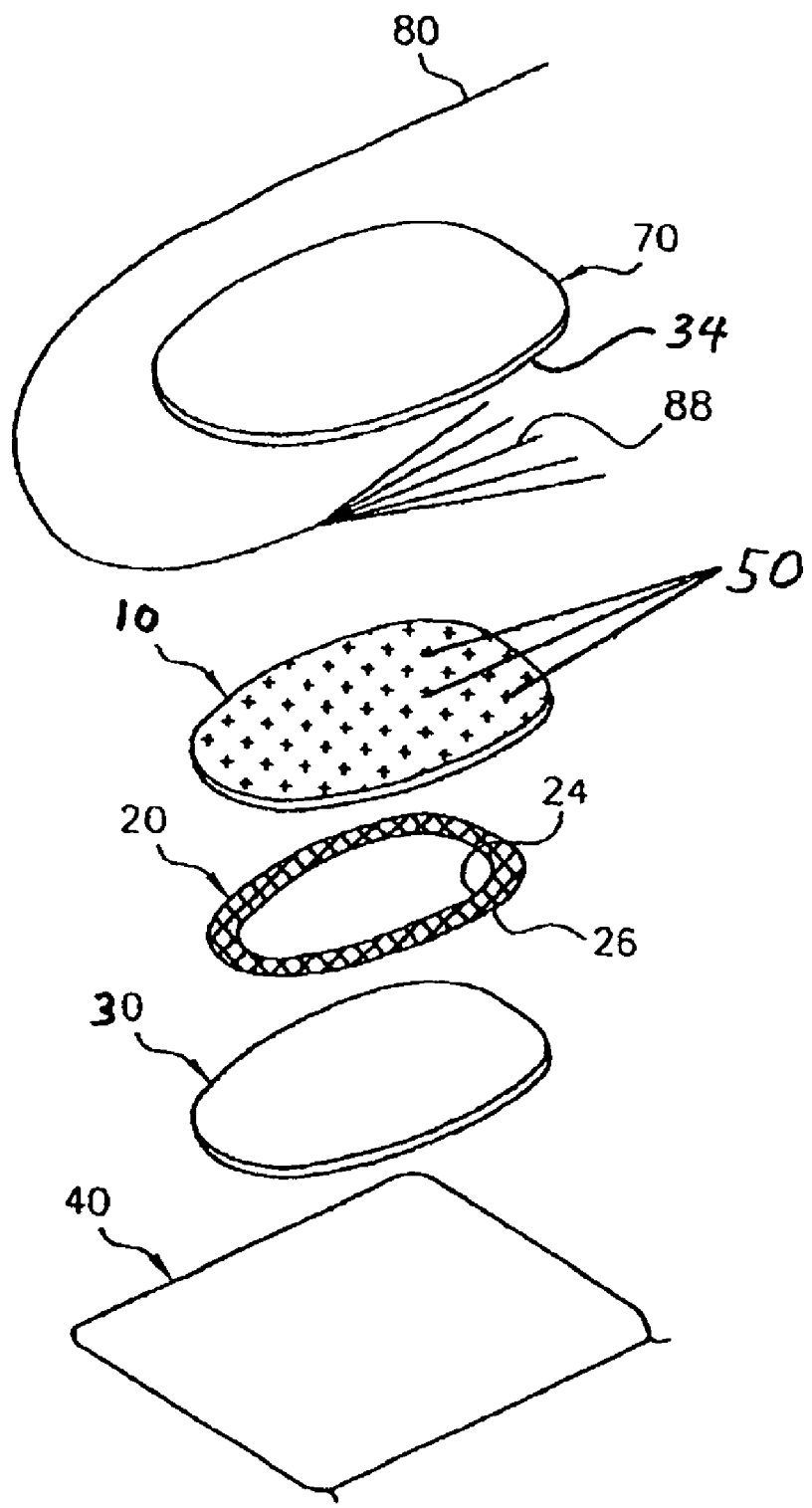
FIG. 2 is a perspective exploded view illustrating the components of a medical electrode according to a second embodiment with an impedance gradient.

Patient contacting layer 30 is in electrical contact with electrode member 10. In a second embodiment, shown in FIG. 2, the medical electrode may further comprise a conductive coating 20 in contact with at least a portion of the bottom face of electrode member 10. One specific example of conductive coating 20 is a silver/silver chloride ink coating. The conductive coating may have a variation or gradient in coverage—and hence in impedance—from center to edge in order to further reduce current density which can result in skin irritation or burning. As one example, disclosed in detail in U.S. Pat. No. 6,600,957 and shown in FIG. 2, the ink coverage is 100% in the area from the center of coating 20 to an inner edge 24. In the area between inner edge 24 and an outer edge 26, the percentage decreases linearly, reaching zero at the outer edge 26.

An impedance gradient may also be formed with a two-layer conductive coating. A conductive coating, such as silver/silver chloride, may be applied to a bottom face of electrode member 10, with the outer perimeter of the coating spaced inwardly from the perimeter of the electrode member 10. The coating may be formed in two layers each of a few microns in thickness with a first layer having an outer perimeter spaced inwardly of the perimeter of the electrode member 10 and a second layer having an outer perimeter spaced inwardly from the perimeter of the first layer. The two layers may be applied successively on electrode member 10 to allow the first layer to dry before applying the second. The second layer may be applied first with the first layer underlying the second layer. The dual layers provide higher electrical conductivity in the area where the layers overlap, with the conductivity stepping down in the single layer and decreasing to the conductivity of a carbon filled polymer of the electrode member 10 in the area outwardly of the coating. The area where the layers overlap, which corresponds to the area of the first layer, may be made substantially equal to the minimum active electrode area prescribed by ANSI/AAMI. For example, the two layers can each have a thickness of about 3 to 5 microns, with a combined thickness in the area of overlap of about six to ten microns. In addition, the outer perimeter of the two layers are advantageously serrated or undulated. This arrangement further decreases the current density by increasing the effective perimeter of the electrode member and, in combination with the use of disconnected conductive regions 50, minimizes the likelihood of skin burns or irritation.

The electrode member 10 may be formed of a thin, flexible sheet of electrically conductive polymer film such as graphite-filled polyvinyl chloride film. The film may also contain carbon black, acetylene black, or other forms of carbon. An example of carbon filled polymer which can be used is commercially available thin carbon filled polyvinyl chloride (PVC).

Figure 3:
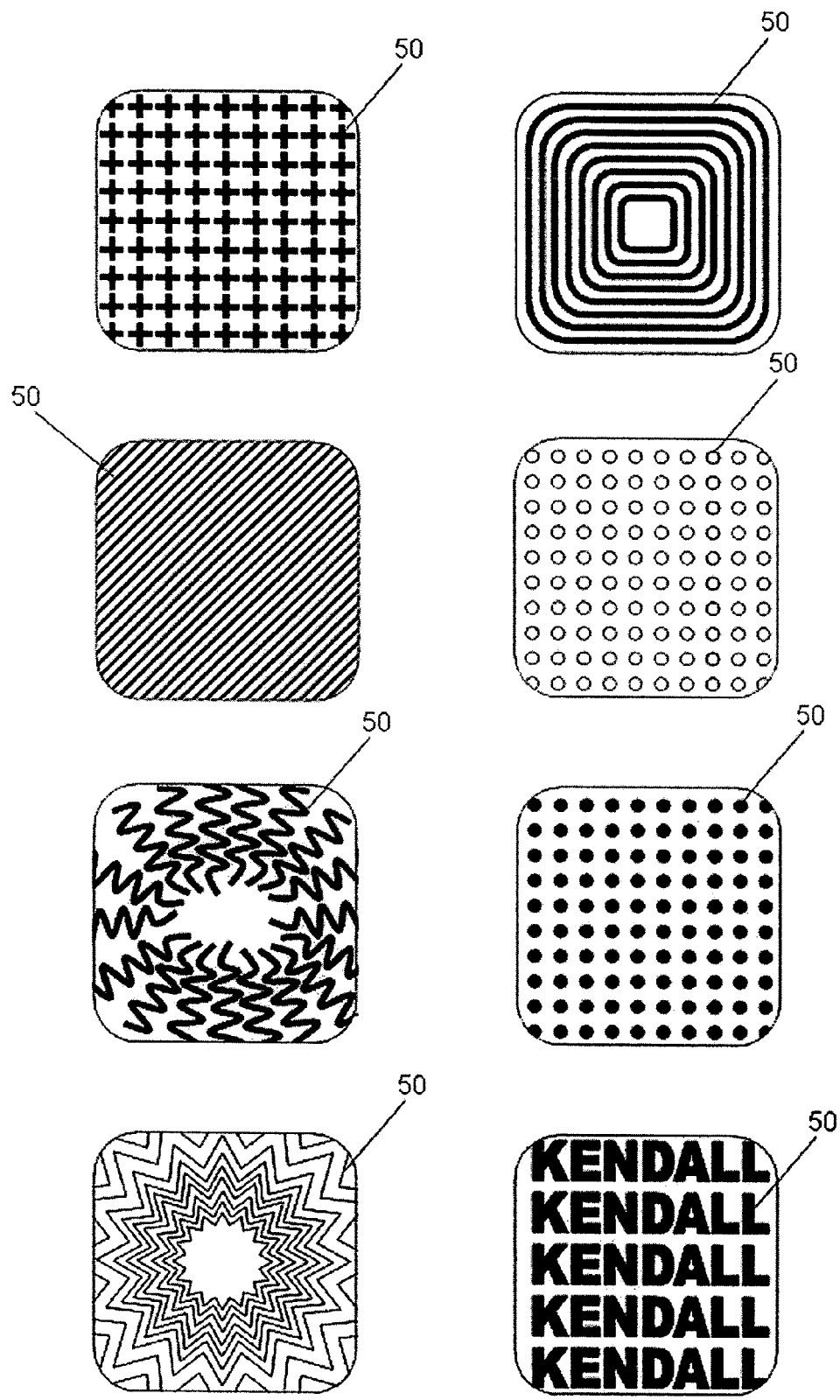
FIG. 3 shows plan views of eight examples of patterns of disconnected regions.

A pattern of disconnected regions of electrically conductive material 50 is in contact with the top face of the electrode member 10. The pattern may comprise separated, disconnected regions of an electrically conductive material 50, such as a conductive ink. The regions 50 may have the shape of stripes, filled polygons, unfilled polygons, filled closed curves, concentric closed curves, unfilled closed curves, letters, logos, and any combination thereof. Examples of such patterns of disconnected regions 50 are shown in FIG. 3. In the embodiment shown in FIG. 1 the pattern is made up of regions of electrically conductive material 50 in the shape of a cruciform or crossed lines, similar to the letter "x". The pattern may cover essentially the entire top face of the electrode member 10, as in the embodiment shown in FIG. 1.

The disconnected regions of electrically conductive material may be formed by printing the electrically conducting material in a discontinuous pattern. Alternatively, the regions may be formed by forming a sheet comprising an electrically conductive material and printing a pattern of electrically non-conducting material on the sheet. The regions not covered by the non-conducting material form the disconnected regions of electrically conductive material. The sheet may then be laminated to the top face of the electrode member 10 to complete the formation of regions 50. As a specific example, forming the sheet of electrically conductive material may comprise flood-coating the top face of electrode member 10 with an electrically conductive fluid, such as a silver/silver chloride ink, and allowing the fluid to dry or otherwise solidify.

An electrical connector 88 is situated in direct contact with the disconnected pattern of electrically conducting material 50. The electrical connector 88 is connected to a conductor which together function to convey electrical signals between the electrode and an apparatus (not shown) such as a defibrillator or electrocardiograph. In the embodiment shown in FIG. 1 the connector 88 is a fanned wire. Another suitable connector may be a metal foil fanned in a similar manner to that of connector 88 in FIG. 1. Other suitable connectors include snaps, rivets, or metal foils well known in the art.

The connector 88 is kept in physical and electrical contact with the disconnected conductive regions 50, and hence with the electrode member 10, by sandwiching it with a cover sheet 70 which is adhered to the top face of the electrode member 10 with an adhesive layer 34. The adhesive layer 34 may be a pressure sensitive adhesive. The cover sheet 70 may be a continuous foam backing sheet without any openings and having a thickness of about 1 mm. In the embodiment shown in FIG. 1, cover sheet 70 extends to the outer dimensions of gel pad 30. Thus, the cover sheet 70 and the gel pad 30 form a single peripheral edge for the electrode once release carrier sheet 40 is removed. In an alternate embodiment, adhesive 34 may be used to additionally secure connector 88 to electrode member 10. Adhesive 34 may comprise a conductive or non-conductive material. By way of example, adhesive 34 may be applied in a stripe across a fanned wire as shown in FIG. 1. Suitable conductive adhesives include hydrogels and epoxies. Suitable non-conductive adhesives include pressure sensitive adhesives.

In the embodiment shown in FIG. 1 the electrode member 10 and the disconnected regions 50 lie essentially in a plane, and connector 88 is held in contact with disconnected conductive regions 50 by cover sheet 70. In an alternate embodiment, electrode member 10, with disconnected conductive regions 50, may be folded over connector 88, thereby enclosing connector 88 and maintaining its contact with conducting regions 50.

Within the pattern of disconnected regions 50, the shapes and sizes of regions and spaces between the regions may be chosen so as to achieve a distribution of electrical current in the electrode which optimizes the electrode impedance for a given application, while also minimizing the effects of high current concentration in some regions of the electrode which could result in patient skin irritation and burning. By way of example, if the sizes of each of the disconnected regions 50 are too small, or their density (number of regions per unit area) is too small, the electrical impedance of the electrode may be unacceptably high due to insufficient metal-to-metal contact between the connector 88 and the disconnected conductive regions 50. Conversely, if the regions 50 are too large or too dense, the electrical impedance of the electrode may result in burning or irritation of the patient's skin. It follows that there is a desired range of patterns (region sizes and densities) that minimize patient skin irritation and burning, while achieving optimal values of overall impedance.

In some applications it is desirable that connector 88 be X-ray transmissive. X-ray transmissive conductors may be formed of metallized carbon fiber tows with an insulating sheath formed of an X-ray transparent material. The carbon fiber tows may be of a size having between 3,000 to 12,000 fibers and metal plated with a metal coating that is about 20% to 50% by weight of the metal plated carbon fiber tow. The higher weight plating on the larger size tows provides improved current carrying capacity for repeated defibrillation pulses. Fiber tows may be made from a polyacrylonitrile precursor and are referred to as pan base carbon fiber and are commercially available from Amoco Performance Products, Inc., Atlanta, Ga. Since the density of the carbon fiber tows is very low as compared to the density of the metal coating, a metal coating of 30% to 40% by weight of the metal plated carbon fiber tow is very thin and is X-ray transparent. The metal coating may be nickel which provides good electrical conductivity and corrosion resistance at moderate cost, but other metals such as copper or silver or gold could be used alone or in combination with the nickel coating.

In electrode applications where X-ray translucency of the connector 88 is not required, the connector 88 can be formed of metal such as copper, tin, silver, or gold. For example, a fanned wire, such as that shown in FIG. 2, may be formed of multi-strand conductors which can be spread out to increase the contact area between the connector 88 and the disconnected regions 50. When metal fanned wire is used, the rest of the electrode remains x-ray transmissive with only the metal fanned wire visible on the x-rays.

Although the invention is illustrated and described herein with reference to specific embodiments, the invention is not intended to be limited to the details shown. Rather, various modifications may be made in the details within the scope and range of equivalents of the claims and without departing from the invention.

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. A medical electrode comprising:
    an electrode member having a top face and a bottom face;
    separated disconnected regions of electrically conductive material in electrical contact with the top face of the electrode member;
    a patient contacting layer disposed on at least a portion of the bottom face of the electrode member; and
    an electrical connector in electrical contact with the separated disconnected regions of electrically conductive material;
    wherein the electrical connector comprises a fanned connector.

2. The electrode of claim 1, wherein the patient contacting layer comprises one or more of an electrically conductive gel layer, a gel pad containing electrically conductive gel, and an electrically conductive adhesive.

3. The electrode of claim 2, wherein the electrically conductive gel layer or adhesive comprise a skin-compatible hydrogel.

4. The electrode of claim 1, further comprising a conductive coating in contact with at least a portion of the bottom face of the electrode member.

5. The electrode of claim 4, wherein an electrical impedance of the conductive coating increases in a direction from a center to edges of the electrode.

6. The electrode of claim 4, wherein the conductive coating comprises a metal and a metal chloride.

7. The electrode of claim 6, wherein the metal is silver and the metal chloride is silver chloride.

8. The electrode of claim 1, further comprising a cover sheet adhered with an adhesive to the electrode member, to the disconnected regions, and to the electrical connector.

9. The electrode of claim 1, wherein the disconnected regions comprise one or more of stripes, unfilled polygons, filled polygons, unfilled closed curves, filled closed curves, concentric closed curves, letters, logos, or any combination thereof.

10. The electrode of claim 9, wherein the filled polygons have the shape of a cruciform.

11. The electrode of claim 1, wherein the electrode member and the disconnected regions of electrically conductive material lie essentially in a plane.

12. The electrode of claim 1, wherein the electrically conductive material is a conductive ink.

13. The electrode of claim 12, wherein the electrically conductive ink is a silver ink.

14. The electrode of claim 1, wherein the electrode member comprises an electrically conductive polymer.

15. The electrode of claim 14, wherein the electrically conductive polymer comprises polyvinyl chloride and one or more forms of carbon black.

16. The electrode of claim 1, wherein the fanned connector comprises metal wires, conductive metal-coated fibers, or both.

17. The electrode of claim 1 further comprising a removable release carrier sheet covering the patient contacting layer and adapted to be removed from the electrode for use of the electrode on a patient.

18. The electrode of claim 1, wherein all components of which the electrode is comprised are such that the electrode is transmissive to X-rays.

19. The electrode of claim 1, wherein the electrode is capable of being disposable.

20. The electrode of claim 1, wherein the electrode is a defibrillation electrode.

21. A method for fabricating a medical electrode configured for high-energy applications, the method comprising the steps of:
    obtaining an electrode member with a top face and a bottom face;
    forming separated disconnected regions of electrically conductive material on the top face of the electrode member;
    adhering a patient contacting layer to the electrode member; and
    securing an electrical connector in contact with the separated disconnected regions of electrically conductive material;
    wherein the step of forming disconnected regions of electrically conductive material comprises the steps of:
    forming a sheet comprising the electrically conductive material, and
    printing a pattern of electrically non-conductive material on the sheet.

22. The method of claim 21, further comprising the step of laminating the sheet to the top face of the electrode member.

23. The method of claim 21, wherein the step of forming a sheet of the conductive material comprises flood-coating the top face of the electrode member with an electrically conductive fluid.

24. A method for fabricating a medical electrode configured for high-energy applications, the method comprising the steps of:
    obtaining an electrode member with a top face and a bottom face;
    forming separated disconnected regions of electrically conductive material on the top face of the electrode member;

adhering a patient contacting layer to the electrode member; and securing an electrical connector in contact with the separated disconnected regions of electrically conductive material;

wherein the step of securing an electrical connector in contact with the disconnected regions of electrically conductive material further comprises the step of fanning strands of the connector and spreading the strands over at least a portion of the disconnected regions of electrically conductive material.

* * * * *